US00PP11119P

United States Patent [19]

Lamis

[11] Patent Number: Plant 11,119

[45] Date of Patent: Nov. 9, 1999

[54] SUGAR MAPLE TREE NAMED 'BAILSTA'

[75] Inventor: Max S. Lamis, McMinnville, Oreg.

[73] Assignee: Bailey Nurseries Inc., St. Paul, Minn.

[21] Appl. No.: 09/018,018

[22] Filed: Feb. 3, 1998

[51] Int. Cl.[6] ..... A01H 5/00

[52] U.S. Cl. ..... Plt./224

[58] Field of Search ..... Plt./224, 216

[56] References Cited

U.S. PATENT DOCUMENTS

| | | | |
|---|---|---|---|
| P.P. 1,311 | 10/1954 | Henderickx | Plt./215 |
| P.P. 2,917 | 8/1969 | Flemer, III | Plt./224 |
| P.P. 3,817 | 12/1975 | Flemer, III | Plt./224 |

*Primary Examiner*—Howard J. Locker

*Attorney, Agent, or Firm*—Burns,Doane,Swecker & Mathis, LLP

[57] ABSTRACT

A new cultivar of Sugar Maple tree (i.e., *Acer saccharum*) is provided that exhibits beautiful thick leathery glossy deep green leaves. The leaf bases also tend to be more truncate than those typical of *Acer saccharum.* The leaves possess a waxy upper surface. The tree is a vigorous grower and exhibits superior performance when exposed to summer heat and wind. Accordingly, good resistance to leaf tatter that is common in Sugar Maple trees is exhibited. The branching habit is substantially symmetrical. Attractive fall leaf coloration in shades of yellow, orange and red generally is exhibited. Also, the winter hardiness is good. The new cultivar is well suited for growing in the landscape as an attractive ornamental shade tree.

3 Drawing Sheets

SUMMARY OF THE INVENTION

The original Sugar Maple tree of the new cultivar was selected on Aug. 12, 1987 from a seedling block of *Acer saccharum* trees growing in production fields of Bailey Nursery Inc. at Yamhill, Oreg. The selection was made on the basis of the distinctive appearance of a single tree of the new cultivar as described hereafter that was discovered while growing among standard *Acer saccharum* trees present in such production fields. The seeds used to plant the production fields was previously collected from *Acer saccharum* trees at the University of Minnesota Landscape Arboretum, Chankassen, Minn. Had I not discovered, studied, and preserved the single tree of the new cultivar it would have been lost to mankind. The tree of the new cultivar initially was designated 0-4-87.

It was found that the new *Acer saccharum* cultivar exhibits the following combination of characteristics:

(a) possesses a more vigorous growth habit than is typical for *Acer saccharum,*
(b) forms glossy leathery deep-lobed deep green leaves having a waxy upper surface and wavy margins which tend to be more truncated than is typical for *Acer saccharum,*
(c) exhibits superior performance when exposed to summer heat and wind,
(d) possesses an upright mounded substantially symmetrical branching habit,
(e) possesses good winter hardiness, and
(f) generally forms attractive fall leaf coloration.

When the new cultivar is compared to the 'Green Mountain' cultivar U.S. Plant Pat. No. 2,339) of *Acer saccharum,* the new cultivar is found to be more vigorous, forms leaves that are more glossy and appear to be protected by a waxy cuticle, better withstands summer heat and wind, and generally forms superior fall leaf coloration.

The new cultivar was first asexually reproduced by budding on seedling *Acer saccharum* during July, 1988 at Yamhill, Oreg. The resulting trees were transplanted in the field in Minnesota during the Spring of 1992. Such trees have performed well and have demonstrated that the distinctive characteristics of the new cultivar are stable and are firmly fixed. The tree characteristics following asexual reproduction were the same as those as the original tree of the new cultivar. Good winter hardiness in combination with the other characteristics has been observed. The fall coloration of the new cultivar has been consistently superior until the fall of 1997 when the leaves of all *Acer saccharum* turned poorly or not at all at the growing area due to unusually warmer weather conditions during late September and early October. Accordingly, the fall leaf coloration can be somewhat variable depending upon the environmental conditions that are encountered. Commonly the typical fall leaf coloration that is observed varies from Orange Group 28B and 28C to Orange-Red Group 30C and 30D.

The superior vigor of the new cultivar was confirmed during the observation of a large number of four-year-old trees of the new cultivar, the 'Green Mountain' cultivar, and standard *Acer saccharum* seedlings growing in Minnesota. Such superior vigor is confirmed by the following tree caliper data that was obtained during such observation:

| Caliper | New Cultivar | 'Green Mountain' Cultivar | Standard *Acer saccharum* Seedlings |
|---|---|---|---|
| 2 inches | 70 percent | 30 percent | 20 percent |
| 1¾ inches | 25 percent | 44 percent | 44 percent |
| 1½ inches | 5 percent | 26 percent | 30 percent |
| 1¼ inches | — | — | 6 percent |

When compared to the 'Bonfire' cultivar U.S. Plant Pat. No. 3,817), the new cultivar of the present invention is hardier, forms generally smaller leaves that are glossier and tend to be thicker and less subject to leaf tattering, and exhibits more yellow and less red in the fall leaves.

The new cultivar of the present invention has been named the 'Bailsta' cultivar and is being marketed under the FALL FIESTA trademark.

BRIEF DESCRIPTION OF THE PHOTOGRAPHS

The accompanying photographs in FIGS. 1, 2, and 4 show, as nearly true as it is reasonably possible to make the same in color illustrations of this character, typical specimens of the plant and plant parts of the new cultivar. FIG. 3 is provided for comparative purposes. The trees depicted in the photographs were grown in the test area of the Hageman farm at Cottage Grove, Minn.

FIG. 1 illustrates during August 1997 a mature tree of the new cultivar at an age of approximately 10 years. The trunk diameter is approximately 5 inches, the height is approximately 20 feet, and the maximum breadth is approximately 15 feet.

FIG. 2 illustrates during August 1997 a typical mature leaf of the new cultivar. The leaf is deeply lobed. The leathery glossy leaf appearance is visible as is the substantially truncate leaf base.

FIG. 3 illustrates during August 1997 for comparative purposes a typical mature leaf of the 'Green Mountain' cultivar (U.S. Plant Pat. No. 1,311). The absence of a glossy leaf appearance, the presence of lobes of a lesser depth, and a less truncate leaf base are apparent when compared to the leaf of FIG. 2.

FIG. 4 illustrates the tree of FIG. 1 during October 1996. Excellent fall coloration in shades of yellow, orange, and red is apparent.

DETAILED DESCRIPTION

The chart used in the identification of colors is that of The Royal Horticultural Society (R.H.S. Colour Chart). Common color terms are to be accorded their ordinary dictionary significance. The description is based on the observation of a test planting of the new variety while grown at Cottage Grove, Minn.

Botanical classification: *Acer saccharum,* cv. 'Bailsta'.

Plant:

*Growth habit.*—Upright, rounded, substantially symmetrical branching habit.

*Size.*—Generally exceeds that of a standard *Acer saccharum* at a given age. For instance, a ten year-old tree has been observed to exhibit a trunk diameter of approximately 5 inches, a height of approximately 20 feet, and a maximum breadth of approximately 15 feet. It is anticipated that a fully mature tree will assume a height of approximately 50 to 75 feet and spread of approximately 50 feet.

Figure 1:
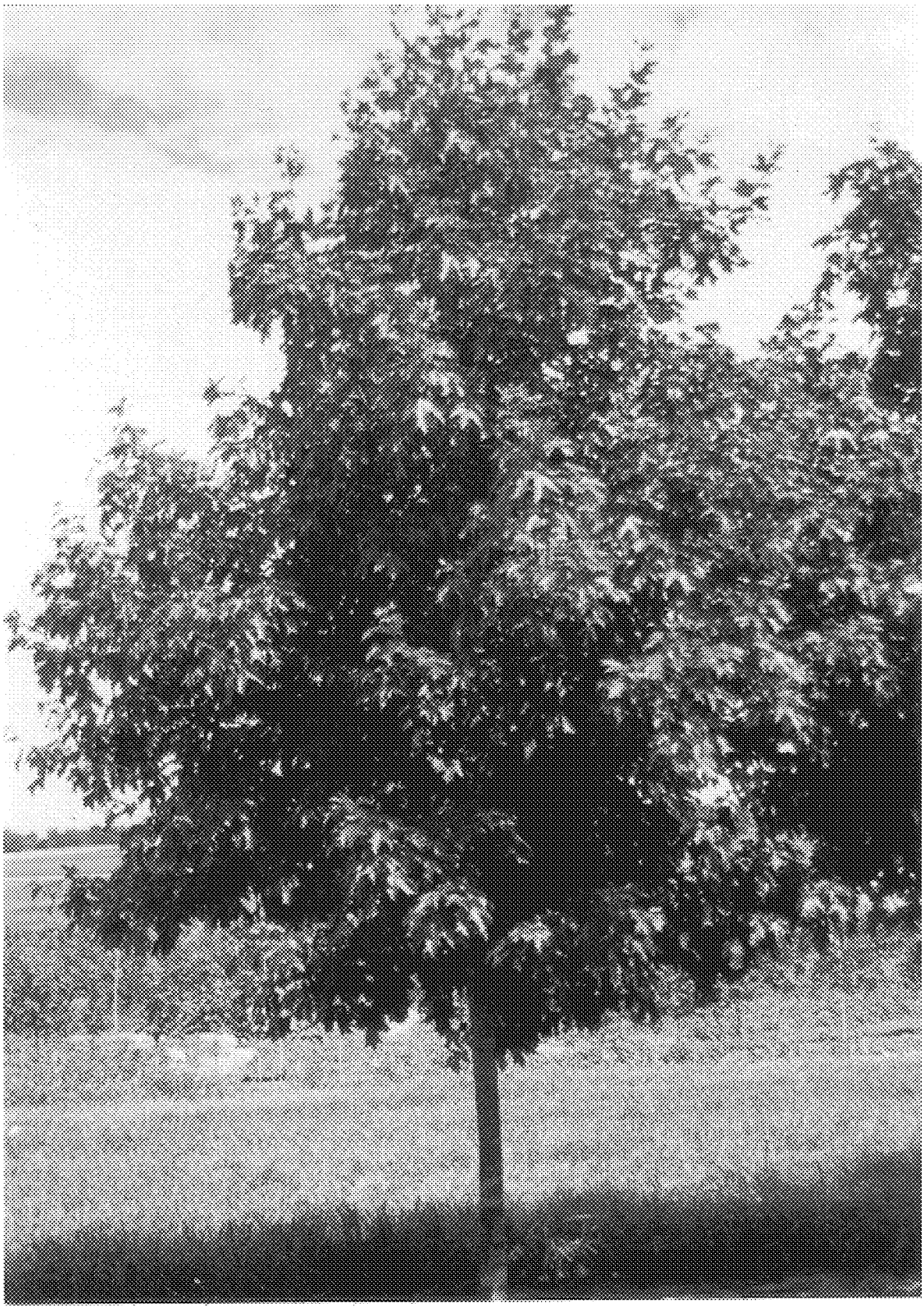
Figure 4:
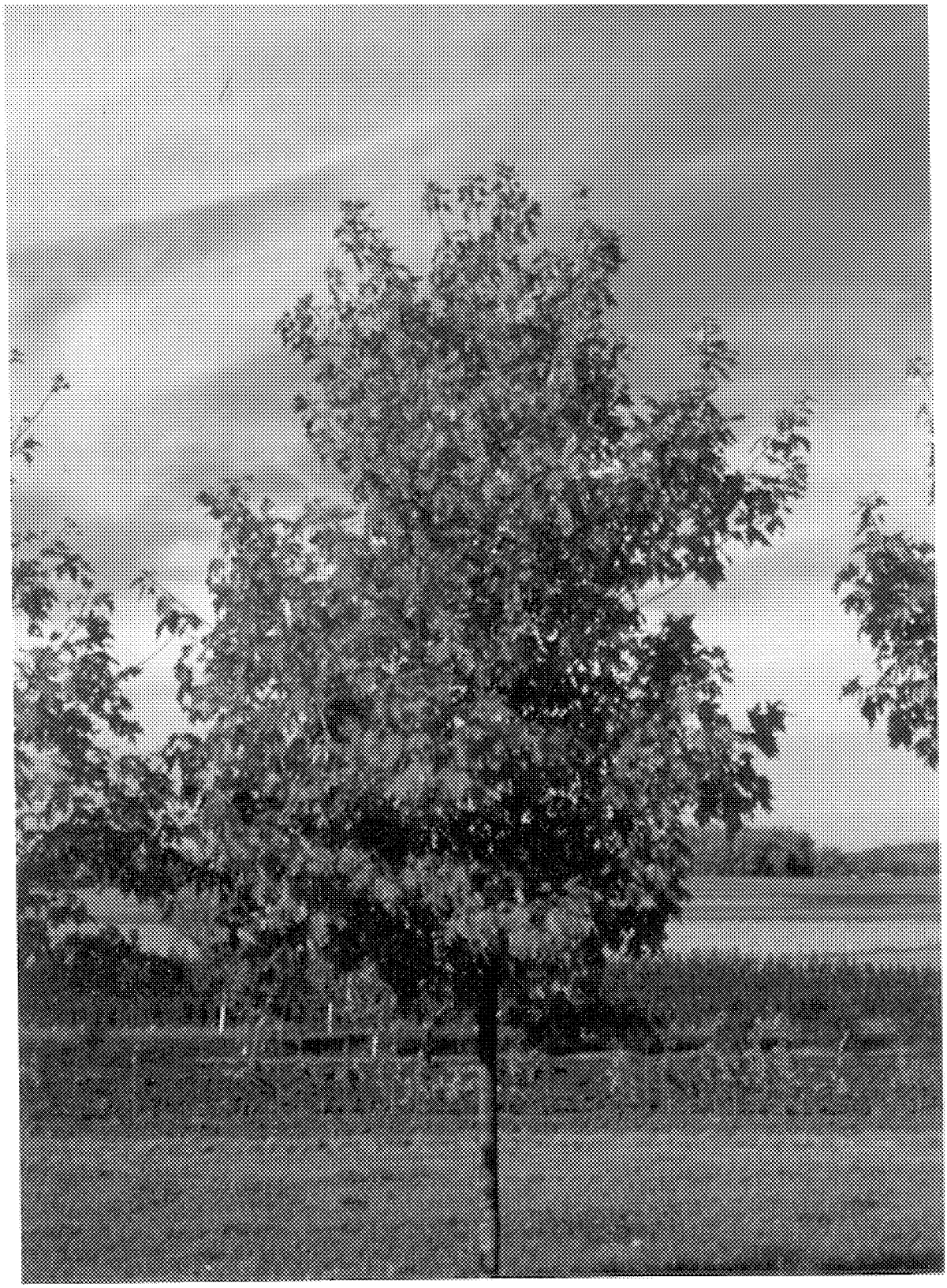

*Bark.*—Dark brown (as illustrated in FIGS. 1 and 4). Commonly is near Grey Group 201D.

*Trunk.*—Generally straight in configuration.

Figure 2:
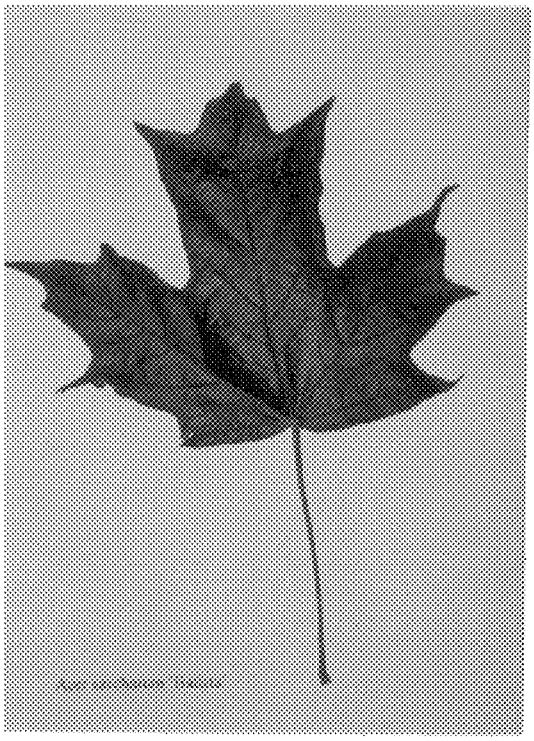
Figure 3:
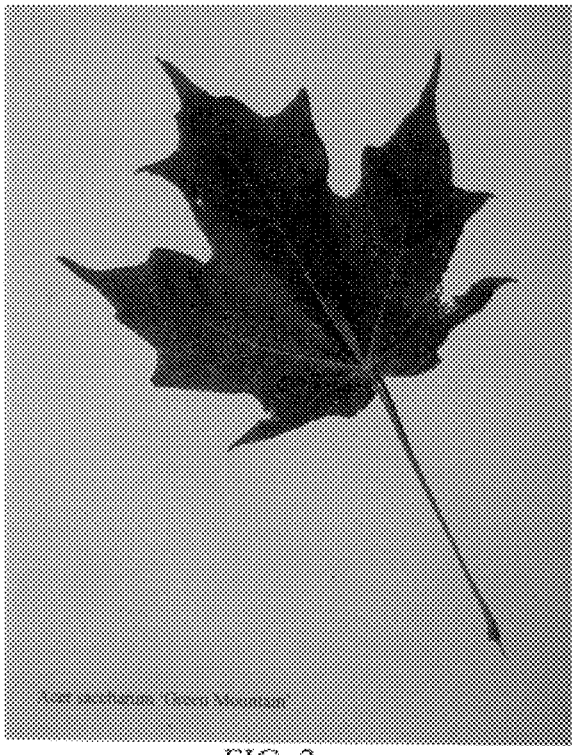

Foliage:

*Shape.*—Thick, deeply-lobed with wavy margins and generally with a more truncate base than is typical for the species (as illustrated in FIG. 2).

*Color.*—During the summer deep green, Green Group 135A to Green Group 135B on the upper surface, and Green Group 138B on the under surface. During the fall generally produces a brilliant display of coloration ranging from yellow, orange, and red as illustrated in FIG. 4.

*Size.*—Commonly larger than is typical of the species under the same growing conditions and commonly approximately 9 to 13 cm. in length and approximately 10 to 15 cm. in width.

*Leaf surface.*—Glossy on upper surface and covered with a thick waxy cuticle or epidermal layer.

Reproductive organs and fruit: Typical of those of Sugar Maple.

Development:

*Vegetation.*—Commonly displays more vigor than is typical for the species as illustrated by a larger caliper and overall tree size at a given age.

*Ability to withstand heat and wind.*—Possesses an uncommon ability to hold up well under summer heat and wind and thereby shows excellent durability and resistance to summer wind and drought. Accordingly, the leaves display a good aesthetic appeal throughout the summer in the substantial absence of leaf tatter.

*Hardiness.*—Perfect winter hardiness has been consistently observed to date.

*Disease resistance.*—No disease problems have been observed to date. For instance, no Sugar Maple verticillium wilt has been observed which is considered to be the most serious disease that attacks the species. Such disease often is present in fully mature trees of the species.

I claim:

1. A new and distinct cultivar of *Acer saccharum* having the following combination of characteristics:

(a) possesses a more vigorous growth habit than is typical for *Acer saccharum,*
(b) forms glossy leathery deep-lobed deep green leaves having a waxy upper surface and wavy margins which tend to be more truncated than is typical for *Acer saccharum,*
(c) exhibits superior performance when exposed to summer heat and wind,
(d) possesses an upright mounded substantially symmetrical branching habit,
(e) possesses good winter hardiness, and
(f) generally forms attractive fall leaf coloration;

substantially as illustrated and described.

* * * * *